United States Patent [19]

Cragoe, Jr. et al.

[11] 4,070,464

[45] Jan. 24, 1978

[54] METHOD OF TREATING AUTOIMMUNE DISEASES

[75] Inventors: Edward J. Cragoe, Jr., Lansdale; Clarence G. Van Arman, Fort Washington, both of Pa.

[73] Assignee: Merck & Co., Inc., Rahway, N.J.

[21] Appl. No.: 748,787

[22] Filed: Dec. 9, 1976

Related U.S. Application Data

[63] Continuation-in-part of Ser. No. 659,443, Feb. 19, 1976, abandoned.

[51] Int. Cl.$^2$ .................... A01N 9/00; A01N 9/22; C07D 265/00; C07D 273/00
[52] U.S. Cl. .................... 424/248.51; 424/248.52; 424/248.56; 424/248.57; 544/71
[58] Field of Search ............ 260/244; 424/248, 659, 424/443, 248.51, 248.52, 248.56

[56] References Cited

U.S. PATENT DOCUMENTS

| | | | |
|---|---|---|---|
| 3,794,734 | 2/1974 | Cragoe et al. | 424/330 |
| 3,798,218 | 3/1974 | Fauran et al. | 260/246 R |
| 3,809,721 | 5/1974 | Schultz et al. | 260/570.9 |
| 3,887,550 | 6/1975 | Beckwith | 260/244 R |

FOREIGN PATENT DOCUMENTS 1,374,294  11/1974  United Kingdom ............ 424/248.51

OTHER PUBLICATIONS

J. Org. Chem. 33(1), 1–8, (1968), McDonogh, et al., "Ring–Chain Tautomerism of Derivatives . . . Ketones,".

Chem. Abst. 72, 111394(n), (1970), Shiri; et al., "Phenoxazine related compounds".

*Primary Examiner*—Albert T. Meyers
*Assistant Examiner*—D. W. Robinson
*Attorney, Agent, or Firm*—William H. Nicholson; Mario A. Monaco

[57] ABSTRACT

3,4-Dihydrospiro-2H-1,3-benzoxazines and pharmaceutical compositions thereof are useful in the treatment of autoimmune diseases.

10 Claims, No Drawings

METHOD OF TREATING AUTOIMMUNE DISEASES

BACKGROUND OF THE INVENTION

This application is a continuation-in-part of copending application U.S. Ser. No. 659,443, filed Feb. 19, 1976, now abandoned.

Multiple sclerosis, allergic encephalomyelitis, and acute necrotizing hemorrhagic encephalopathy are members of a group of disease entities the etiology of which is generally believed to be an autoimmune response. It is further believed by those skilled in the art that experimental allergic enchephelomyelitis is a good laboratory model of these autoimmune diseases. Waksman, *International Archives of Allergy and Applied Immunology,* Supplementum ad vol. 14, 1959, (S. Karger, Basel, and New York; Paterson, *J. Chron. Dis.,* 26, 119–126 (1973); and Mackay et al., *Clin. exp. Immunol.,* 15, 471–482 (1973); Levine et al., *Science,* 146, 1681-2 (1964).

Surprisingly, it has been found that certain 3,4-dihydrospiro-2H-1,3-benzoxazines with diuretic and antiinflammatory activity as described in United States Patent Application Ser. Nos. 571,462 (now abandoned) and 659,442 are potent inhibitors of the progress of experimental allergic encephelomyelitis in the rat, and are therefore useful in the treatment of autoimmune diseases such as multiple sclerosis, allergic encephalomyelitis, and acute necrotizing hemorrhagic encephalopathy.

It is therefore an object of this invention to provide a method of treating autoimmune diseases such as multiple sclerosis, allergic encephalomyelitis and acute necrotizing hemorrhagic encephalopathy by the administration of an effective amount of a 3,4-dihydrospiro-2H-1,3benzoxazine hereinafter described.

DETAILED DESCRIPTION OF THE INVENTION

The compounds active in the novel method of treatment of this invention have the following structural formula:

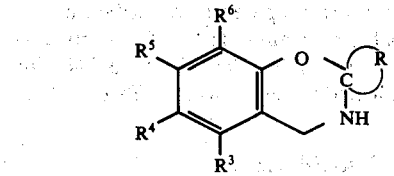

wherein
$R^3$ is
1. hydrogen,
2. methyl,
3. chloro, or
4. methoxy;

$R^4$ is
1. halo, such as chloro, bromo, or iodo,
2. lower alkyl, especially $C_{1-7}$ alkyl, either straight or branched chain, such as methyl, propyl, isopropyl, butyl, t-butyl, secbutyl, pentyl, isopentyl, hexyl, or heptyl,
3. adamantyl;

$R^5$ is 1. hydrogen,
2. lower alkyl, especially $C_{1-7}$ alkyl, either straight or branched chain,
3. lower alkoxy, especially $C_{1-5}$ alkoxy, either straight or branched chain such as methoxy, ethoxy, propoxy, butoxy or pentoxy, or
4. halo, such as fluoro, chloro, bromo, or iodo;

$R^6$ is
1. halo, such as chloro, bromo or iodo;
2. lower alkyl, especially $C_{1-7}$ alkyl, either straight or branched chain,
3. lower alkylthio, especially $C_{1-3}$ alkylthio, or
4. trifluoromethyl;

$R^5$ and $R^6$ taken together is $-N=CH-CH=CH-$;

$$\diagdown_R$$

is
1. a spiro-carbocycle of 5,6 or 10-17 members, either unsubstituted or substituted with
  a. lower alkyl, especially $C_{1-7}$ alkyl,
  b. lower alkoxy, especially $C_{1-5}$ alkoxy,
  c. phenyl, either unsubstituted or substituted with lower alkoxy, especially $C_{1-5}$ alkoxy,
  d. lower alkanoyloxy, especially $C_{2-5}$-alkanoyloxy;
2. a 6-membered spiro-heterocycle containing 1 or 2 hetero atoms selected from oxygen, sulfur and nitrogen such as spiro-tetrahydropyran, spiro-tetrahydrothiapyran, spiro-3,5-dithiacyclohexane, spiro-piperidine, wherein the nitrogen heteroatom can be substituted with
  a. lower alkyl, especially $C_{1-7}$ alkyl,
  b. phenyl-lower alkyl, especially phenyl-$C_{1-3}$ alkyl,
  c. lower alkanoyl, especially $C_{2-5}$ alkanoyl,
3. spiro-polycycloalkyl of 6-15 members such as spiro-nortricyclane, or spiro-adamantane, or

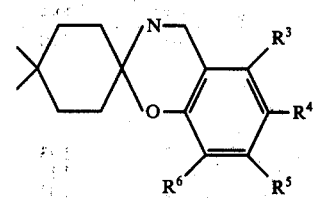

(4)

wherein $R^3$, $R^4$, $R^5$, and $R^6$ are as previously defined.

A preferred aspect of the compounds active in the novel method of treatment of this invention is that of Formula I, wherein $R^3$ and $R^5$ are both hydrogen.

A more preferred aspect of these compounds is that of Formula I, wherein $R^3$ and $R^5$ are hydrogen, $R^4$ is $C_{1-7}$ alkyl, and $R^6$ is halo.

An even more preferred aspect of these compounds is that of Formula I, wherein $R^3$ and $R^5$ are hydrogen, $R^4$ is $C_{1-7}$ alkyl, particularly branched alkyl such as t-butyl, $R^6$ is halo and $$\diagdown_R$$

is spiro-tetrahydrothiapyran, spiro-cyclohexane or spiro-piperidine.

The above defined compounds are useful in the treatment of autoimmune disease as measured by their ability to inhibit the progress of experimental allergic encephelomyelitis in rats. The method used was as follows:

Reference: Lipton, M. M. and J. Freund: *J. Immunology* 71, 98, (1953); M. E. Rosenthale and C. L. Nagra: *Proc. Soc. Exp. Biol. Med.*, 125, 149 (1967). Test Object: Rat, female, Lewis strain, 160–180 gms. Procedure: Groups of six rats each are injected subcutaneously in the distal third of the tail with 0.1 ml. of an emulsion containing 200 mg. of homologous spinal cord and 2.5 mg. of Mycobacterium butyricum in each ml. Compounds to be tested may be given either orally or parenterally, suspended or dissolved in either 0.5% Methocel or physiological saline, and are given once daily beginning on day minus one through day 13.

An ascending motor paralysis appears about day 10. Quantitation of the degree of paralysis is made on day 14 by the scoring system:

0 — Not affected, normal activity, body weight gain and general appearance
1 — No paralysis but loss of body weight and lack of grooming
2 — Paralysis on one hind leg only
3 — Paralysis in both hind legs with ability to move about using forepaws
4 — Generalized paralysis, moribund
5 — Death Drug effects expressed as percent inhibition are determined by:

$$100 \times \frac{\text{Paralysis score of controls} - \text{Paralysis score of treated}}{\text{Paralysis score of controls}}$$

Amount of Compound Required: 100 to 1000 mg., depending on activity.
Solubility Requirements: None
Standard Compounds: None Typical results are as follows:

| "L" Number & Chemical Name | Dose mg/kg | Change in Body Weight grams | Score | Percent Inhibition |
|---|---|---|---|---|
| L-629,051-00V-12 6-t-butyl-8-chloro-spiro[cyclohexane-1,2'-(3',4'-dihydro)-2H',1',3'-benzoxazine | 25 | −49 | 3.00 | 25.0 |
| L-629,632-00C-02 6'-t-Butyl-8'-iodo-spiro[cyclohexane-1,2'-(3',4'-dihydro)-2'H-1',3'-benzoxazine] | 3 | −13 | 1.83 | 37.7 |
|  | 6 | −12 | 1.17 | 59.9 |
|  | 12 | −8 | 1.33 | 57.8 |
|  | 24 | +2* | 1.50 | 53.9 |
| L-630-155-00C-01 6'-t-Butyl-8'-iodo-spiro[tri-cyclo(2.2.1.0$^{2,6}$)-heptene-3,2'-(3',4'-dihydro)-2'H-1',3'-benzoxazine] | 10 | −10 | 1.00 | 63.6 |
| L-630,157-00V-01 6'-t-Butyl-8'-iodo-spiro[cyclo-dodecane-1,2'-(3',4'-dihydro)-2'H-1',3'-benzoxazine] | 10 | −10 | 1.50 | 45.4 |
| L-630,555-00S-01 6'-t-Butyl-8'-iodo-spiro[adamantane-2,2'-(3',4'-dihydro)-2'H'-1',3'-benzoxazine] | 10 | −17 | 1.83 | 33.5 |
| L-631,035-00C-01 6'-t-Butyl-8'-iodo-spiro[tetra-hydrothiopyran-4,2'-(3',4'-dihydro)-2H-1',3'-benzoxazine] | 10 | −11 | 1.50 | 45.5 |
| L-630,149-00V-01 1-Methyl-6'-t-butyl-8'-iodo-spiro[piperidine-4,2'-(3',4'-di- | 2.5 | −20 | 2.33 | 15.3 |
|  | 5 | −6 | 1.17* | 57.5* |
|  | 10 | +1* | 0.5 * | 81.8* |

-continued

Typical results are as follows:

| "L" Number & Chemical Name | Dose mg/kg | Change in Body Weight grams | Score | Percent Inhibition |
|---|---|---|---|---|
| hydro)-2'H,1',3'-benzoxazine] | 10 | −4 | 1.17 | 70.7 |

*Statistically significant P ≦ 0.05

The compounds active in the novel method of treatment of this invention can be administered in a wide variety of therapeutic dosage forms in conventional vehicles for systemic administration as, for example, by oral administration in the form of tablets, capsules, solutions, or suspensions, or by intravenous injection. The daily dosage of the products may be varied over a wide range varying from 50 to 2,000 mg. The compositions are preferably provided in the form of scored tablets containing 5, 10, 25, 50, 100, 150, 250, and 500 milligrams of the active ingredient for the symptomatic adjustment of the dosage to the patient to be treated. An effective amount of the drug is ordinarily supplied at a dosage level of from about 1 mg. to about 50 mg./kg. of body weight per day. Preferably the range is from about 1 mg. to 7 mg./kg. of body weight per day. These dosages are well below the toxic or lethal dose of the product. Capsules containing the products of this invention can be prepared by mixing a spiro-benzoxazine of this invention with lactose and magnesium stearate, calcium stearate, starch, talc, or other carriers, and placing the mixture in gelatin capsule. Tablets may be prepared by mixing the active ingredient with conventional tableting ingredients such as calcium phosphate, lactose, corn starch or magnesium stearate. The liquid forms in which the active ingredients may be incorporated include suitable flavored suspending or dispersing agents such as the synthetic and natural gums, for example, tragacanth, acacia, methylcellulose, and the like. Other dispersing agents which may be employed include glycerin and the like. For parenteral administration sterile suspensions and solutions are desired. Isotonic preparations which generally contain suitable preservative are employed when intravenous administration is desired.

The compounds active in the novel method of treatment of this invention are prepared as described in the following examples from starting materials described in the literature such as U.S. Pat. Nos. 3,794,734; 3,809,721; and 3,864,401; and British Patent No. 1,374,294.

EXAMPLE 1

3,4-Dihydro-6-(1,1-dimethylethyl)-8-iodospiro[2H-1,3-benzoxazine-2,4'-tetrahydrothiopyran]

A mixture of 2-aminomethyl-4-(1,1-dimethylethyl)-6-iodophenol (3.0 g., 0.01 mole), tetrahydrothiopyran-4-one (1.18 g., 0.01 mole), and benzene (100 ml.), is refluxed under a Dean-Stark trap for 4 hr. The solvent is evaporated, and the residue is crystallized from ethanol to obtain 3,4-dihydro-6-(1,1-dimethylethyl)-8-iodospiro[2H-1,3-benzoxazine-2,4'-tetrahydrothiopyran], (2.5 g.), m.p. 123°–124° C.

Following the procedure substantially as described in Example 1, but substituting for the 2-aminomethyl-4-(1,1-dimethylethyl)-6-iodophenol and tetrahydrothiopyran-4-one used therein, equimolar amounts of compounds of Formula II and of Formula III, respectively, identified in Table I, there are produced the products of Formula I, also identified in Table I, in accordance with Reaction Scheme I.

TABLE I

| R³ | R⁴ | R⁵ | R⁶ | O=C⟨R⟩ | m.p. (° C.) |
|---|---|---|---|---|---|
| H— | (CH₃)₃C— | H— | I— |  | 100–101 |
| H | (CH₃)₃C— | H | Cl— |  | 107–108 |
| H | (CH₃)₃C— | H | I— |  | 171–172 |
| H | (CH₃)₃C— | H | I— |  | 108–109 |
| Cl | Cl | H | Cl |  | 171.5–172.5 |
| CH₃ | Cl— | C₂H₅— | Cl |  | |
| CH₃ | Br | CH₃ | Br |  | |
| H | (CH₃)₃C— | H | I |  | |

TABLE I-continued

| R³ | R⁴ | R⁵ | R⁶ | O=C⟨R⟩ | m.p. (° C.) |
|---|---|---|---|---|---|
| H | (CH₃)₃C— | H | I |  | |
| H | (CH₃)₃C— | H | I |  | |
| H | (CH₃)₃C— | H | I |  | |
| H | (CH₃)₃C— | H | I |  | |

EXAMPLE 2

3,4-Dihydro-6-(1,1-dimethylethyl)-8-iodo-1'-methylspiro[2H-1,3-benzoxazin-2,4'-piperidine]

A mixture of 2-aminomethyl-4-(1,1-dimethylethyl)-6-iodophenol (6.0 g., 0.02 mole), 1-methyl-4-piperidone (2.24 g., 0.02 mole), acetic acid (2 ml.) and benzene (100 ml.) is refluxed under a Dean-Stark trap for 4 hrs. The clear yellow solution then is washed with 2% sodium hydroxide solution, water and salt brine and dried (MgSO₄). The residue that remains after evaporation of the benzene is crystallized from ethanol to obtain 3,4-dihydro-6-(1,1-dimethylethyl)-8-iodo-1'-methylspiro[2H-1,3-benzoxazin-2,4'-piperidine], (4.6 g.), m.p. 155°–156.5° C.

Following the procedure substantially as described in Example 2, but substituting for the 2-aminomethyl-4-(1,1-dimethylethyl)-6-iodophenol and 1-methyl-4-piperidone used therein, equimolar amounts of compounds of Formula II and of Formula III respectively, identified in Table II, there are produced the products of Formula I, also identified in Table II, in accordance with Reaction Scheme I.

TABLE II

| R³ | R⁴ | R⁵ | R⁶ | O=C⟨R⟩ | m.p. (° C.) |
|---|---|---|---|---|---|
| H | (CH₃)₃C— | H | Cl |  | 135–137 |
| H | (CH₃)₃C— | H | I |  | 141–142 |
| H | (CH₃)₃C— | H | I |  | 135–136.5 |
| H | (CH₃)₃C— | H | I | 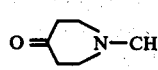 | 138–139 |
| H | (CH₃)₃C— | H | I |  | 165–166 |
| CH₃— | CH₃— | CH₃— | CH₃— | 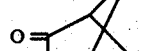 | 117–119 |
| CH₃— | Cl— | CH₃— | Cl | 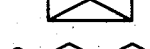 | 98–100 |

TABLE II-continued

| $R^3$ | $R^4$ | $R^5$ | $R^6$ | O=C-R | m.p. (° C.) |
|---|---|---|---|---|---|
| H | $(CH_3)_3C-$ | H | I | O=⟨N-COCH_3⟩ | 155-160 |
| H | $(CH_3)_3C-$ | H | I | O=⟨-OCCH_3⟩ (O) | Glass |
| $OCH_3$ | Cl | $OCH_3$ | Cl | O=⟨ ⟩ | 99-100 |

EXAMPLE 3

3,4-Dihydro-6-(1,1-dimethylethyl)-8-trifluoromethyl-spiro[2H-1,3-benzoxazine-2,2'-tricyclo(3.3.1.1$^{3,7}$)decane]

Step A: Preparation of 2-trifluoromethyl-4-(1,1-dimethylethyl)phenol

A mixture of 2-trifluoromethylphenol (25 g., 0.15 moles), tert-butyl alcohol (12 g., 0.16 mole), trifluoroacetic acid (100 ml.) and 96% sulfuric acid (2 ml.) is stirred at about 20° C. for 48 hours. The mixture then is evaporated as far as possible under reduced pressure at 35°-40° C. The residue is dissolved in benzene (500 ml.) and the solution is washed with water, saturated NaHCO$_3$ solution and saturated salt brine and dried over anhydrous MgSO$_4$. The dried solution is again evaporated under reduced pressure and the temperature is finally raised to 140°-145° C. under 65 mm. pressure to remove unchanged 2-trifluoromethylphenol. The residue is distilled at 65 mm. after collecting a small forerun (75% unchanged starting phenol and 25% product), 2-trifluoromethyl-4-(1,1-dimethylethyl)phenol (13.6 g.) is collected at 120°-132° C. as a pale pink oil that is 98% pure by gas liquid chromatography analysis and can be used directly in the next step.

Step B: Preparation of 2-aminomethyl-4-(1,1-dimethyl-ethyl)-6-trifluoromethylphenol 2-Trifluoromethyl-4-(1,1-dimethylethyl)phenol (15.6 g., 0.062 mole) is dissolved in a mixture of glacial acetic acid (200 ml.) and 96% sulfuric acid (150 ml.). The mixture is stirred and finely powdered N-hydroxymethyl-2-chloroacetamide (8 g., 0.065 mole) is added in small portions at 20°-25° C. Stirring then is continued for 5 hours after which the mixture is poured into water (3 l.). The 2-(2-chloroacetamidomethyl)-4-(1,1-dimethylethyl)-6-trifluoromethylphenol that separates is collected and dried by suction to obtain a solid (19 g., m.p. about 85°-100° C.).

The solid, the 2-chloroacetyl derivative of 2-aminomethyl-4-(1,1-dimethylethyl)-6-trifluoromethylphenol is dissolved in a mixture of ethanol (75 ml.) and 12 N hydrochloric acid (25 ml.) The mixture is refluxed for 5 hours, cooled to 20° C. and diluted with 12 N hydrochloric acid (150 ml.). Upon cooling to −20° C., the product separates (14 g.). It is crystallized from ethanol-12 N hydrochloric acid (1:4) to obtain pure 2-aminomethyl-4-tertbutyl-6-trifluoromethylphenol hydrochloride, m.p. 202°-204° C. This material is added to 500 ml. of warm water and treated with excess ammonium hydroxide. The precipitate is collected, washed with water, and air dried to give the free base, m.p. about 148° C.

Step C: Preparation of 3,4-dihydro-6-(1,1-dimethylethyl)-8-trifluoromethyl-spiro[2H-1,3-benzoxazine-2,2'-tricyclo(3.3.1.1$^{3,7}$)decane]

A solution of 2-aminomethyl-4-(2,2-dimethylethyl)-6-trifluoromethylphenol (1.24 g., 0.005 mole), 2-oxotricyclo(3.3.1.1$^{3,7}$)decane (0.75 g., 0.005 mole) and acetic acid (0.25 ml.) in dry benzene (50 ml.) is refluxed under a constant water separator for 3 hr. The solution is cooled, washed with 2% sodium hydroxide solution, water and salt brine and then dried (MgSO$_4$) and evaporated under reduced pressure. The solid residue (1.2 g.) is crystallized from hexane to obtain 3,4-dihydro-6-(1,1-dimethylethyl)-8-trifluoromethylspiro[2H-1,3-benzoxazine-2,2'-tricyclo(3.3.1.1$^{3,7}$)decane] (0.65 g.), m.p. 125°-126.5° C.

EXAMPLE 4

3,4-Dihydro-6-(1,1-dimethylethyl)-8-(methylthio)-spiro[2H-1,3-benzoxazine-2,2'-tricyclo(3.3.1.1$^{3,7}$)decane]

Step A: Preparation of 2-(methylthio)-4-(1,1-dimethylethyl)phenol

A mixture of 37.5 g. (0.25 mole) of 4-(1,1-dimethylethyl)phenol, 50 ml. of 70% perchloric acid and 40 ml. of phosphorus oxychloride was cooled to 0° C. and treated with 18.0 ml., (19.5 g., 0.25 mole) of dimethyl sulfoxide dropwise with vigorous stirring. Stirring was continued at 0° C. for 2 hour, and room temperature for 16 hours. The mixture was poured onto ice. The precipitate was collected on a filter, washed with ice-water, sucked dry, and washed with ether. The filter cake was added to 500 ml. of saturated potassium chloride solution and refluxed 4 hours. After standing at room temperature overnight, the oily product was extracted into ether, washed with water, saturated sodium chloride solution, dried, and evaporated to dryness to give 42 g. of 2-(methylthio)-4-(1,1-dimethylethyl)phenol.

Step B: Preparation of 2-aminomethyl-4-(1,1-dimethylethyl)-6-(methylthio)-phenol A cold solution of (5.3 g., 0.027 mole) of the phenol from Step A, in 150 ml. of acetic acid and 10 ml. of sulfuric acid was treated with 3.32 g. (0.027 mole) of N-hydroxymethyl-2-chloroacetamide portionwise over about 15 minutes and was stirred for 16 hours at room temperature. The mixture was poured into 1 liter of cold water. The precipitated gum was extracted into ether and washed three times with water and saturated sodium chloride solution and evaporated to dryness. The residue was refluxed with 30 ml. of ethanol and 15 ml. of hydrochloric acid for 4 hours. The mixture was evaporated to dryness and the residue was triturated with ether, collected and recrystallized from a mixture of 10 ml. of ethanol and 12 ml. of ether to give 3.5 g. of the hydrochloride salt of the product; m.p. 179°–181° C.

This salt was added to 100 ml. of water and treated with excess ammonium hydroxide to give 2-aminomethyl-4-(1,1-dimethylethyl)-6-methylthiophenol, m.p. 127°–131° C.

Step C: Preparation of 3,4-dihydro-6-(1,1-dimethylethyl)-8-(methylthio)-spiro[2H-1,3-benzoxazine-2,2'-tricyclo(3.3.1.1.$^{3,7}$)decane]

Employing the procedure of Example 3, Step C, but substituting for the 2-aminomethyl-4-(1,1-dimethylethyl)-6-trifluoromethylphenol used therein, an equimolar amount of 2-aminomethyl-4-(1,1-dimethylethyl)-6-(methylthio)phenol, there is produced 3,4-dihydro-6-(1,1-dimethylethyl)-8-(methylthio)spiro[2H-1,3-benzoxazine-2,2'-tricyclo(3.3.1.1$^{3,7}$)decane], m.p. 162°–164° C.

EXAMPLE 5

3,4-Dihydro-6,8-diiodospiro[2H-1,3-benzoxazine-2,2'-tricyclo(3.3.1.1.$^{3,7}$)decane]

Step A: Preparation of 2-aminomethyl-4,6-diiodophenol

Iodine monochloride (4.95 g., 0.03 mole) was added rapidly to a stirred solution of 1.6 g. (0.013 mole) of 2-aminomethylphenol in 100 ml. of water and 1.5 ml. of hydrochloric acid. After 2½ hours at room temperature, the mixture was cooled to −10° C. and filtered. The filter cake was washed with water and concentrated hydrochloric acid and recrystallized from a mixture of 40 ml. of 95% ethanol, 50 ml. of water, and 4 ml. of hydrochloric acid to give 4.5 g. of the hydrochloride salt, m.p. 215°–217° C.

Solution in about 500 ml. of water and addition of excess ammonium hydroxide provided 2-aminomethyl-4,6-diiodophenol.

Step B: Preparation of 3,4-dihydro-6,8-diiodospiro[2H-1,3-benzoxazine-2,2'-tricyclo(3.3.1.1.$^{3,7}$)decane]

Employing the procedure of Example 3, Step C, but substituting for the 2-aminomethyl-4-(1,1-dimethylethyl)-6-trifluoromethylphenol used therein, an equimolar amount of 2-aminomethyl-4,6-diiodophenol, there is produced 3,4-dihydro-6,8-diiodospiro2H-1,3-benzoxazine-2,2'-tricyclo(3.3.1.1.$^{3,7}$)decane].

EXAMPLE 6

3,4-Dihydro-6-(1-methylethyl)-8-iodospiro[2H-1,3-benzoxazine-2,2'-tricyclo(3.3.1.1.$^{3,7}$)decane]

Step A: Preparation of 2-iodo-4-(1-methylethyl)phenol

A solution of 27.2 g. (0.20 mole) of 4-(1-methylethyl)phenol in 100 ml. of acetic acid was stirred vigorously while 32.5 g. (0.20 mole) of iodine monochloride in 50 ml. of acetic acid was added slowly. The mixture was refluxed for six hours, cooled, and poured into 1 liter of water containing a little sodium bisulfite. The crude oily product that separated was extracted into ether and washed well with water and saturated sodium chloride solution, dried and concentrated to dryness. The residue was distilled under reduced pressure to give 26.1 g. of 2-iodo-4-(1-methylethyl)phenol, b.p. 137°–140° C./15 mm Hg.

Step B: Preparation of 2-aminomethyl-4-(1-methylethyl)-6-iodophenol

Employing the procedure of Example 4, Step B, but substituting for the 2-methylthio-4-(1,1-dimethylethyl)-phenol, an equimolar amount of 2-iodo-4-(1-methylethyl)phenol, there is produced 2-aminomethyl-4-(1-methylethyl)-6-iodophenol hydrochloride, m.p. 211°–212° C., and the free base thereof.

Step C: Preparation of 3,4-dihydro-6-(1-methylethyl)-8-iodospiro[2H-1,3-benzoxazine-2,2'-tricyclo(3.3.1.1.$^{3,7}$)decane]

Employing the procedure of Example 3, Step C, but substituting for the 2-aminomethyl-4-(1,1-dimethylethyl)-6-trifluoromethylphenol used therein, an equimolar amount of 2-aminomethyl-4-(1-methylethyl)-6-iodophenol, there is produced 3,4-dihydro-6-(1-methylethyl)-8-iodospiro[2H-1,3-benzoxazine-2,2'-tricyclo(3.3.1.1.$^{3,7}$)decane].

EXAMPLE 7

3,4-Dihydro-6-[1-tricyclo(3.3.1.1.$^{3,7}$)decyl]-8-iodospiro[2H-1,3-benzoxazine-2,2'-tricyclo(3.3.1.1.$^{3,7}$)decane]

Step A: Preparation of 2-aminomethyl-4-[1-tricyclo(3.3.1.1$^{3,7}$-decyl]phenol hydrochloride N-hydroxymethyl-2-chloroacetamide (10.2 g., 0.083 mole) was added to a mixture of 19 g. (0.083 mole) of 4-(1-tricyclo[3.3.1.1.$^{3,7}$]decyl)phenol in 50 ml. of sulfuric acid and 500 ml. of acetic acid. After stirring at room temperature for 3 hours, the mixture was poured into 3 liters of water with stirring. The precipitate was refluxed with 75 ml. of ethanol and 25 ml. of concentrated hydrochloric acid for 3 hours. After cooling −20° C., the precipitate was collected to give 12 g. of 2-aminomethyl-4-[1-tricyclo(3.3.1.1.$^{3,7}$)decyl]phenol hydrochloride, m.p. 272°–274° C.

Step B: Preparation of 2-aminomethyl-4-[1-tricyclo(3.3.1.1.$^{3,7}$)decyl]-6-iodophenol The amine hydrochloride from Step A (2.93 g., 0.01 mole) was dissolved in 600 ml. of hot water, cooled to 40° C. and 1.64 g. of iodine monochloride in 3N HCl (8 ml) was stirred in rapidly. After stirring 2 hours, the mixture was let stand overnight. After cooling to 0° C., the precipitate was collected and recrystallized from 75 ml. of ethanol and 20 ml. of concentrated hydrochloric acid to give 3.3 g. of 2-aminomethyl-4-[1-tricyclo(3.3.1.1$^{3,7}$)decyl]-6-iodophenol hydrochloride, m.p. 232°–233° C.

This is converted to the free base by solution in 1 l. of water and addition of excess ammonium hydroxide.

Step C: Preparation of 3,4-dihydro-6-[1-tricyclo(3.3.1.1.$^{3,7}$)decyl]-8-iodospiro[2H-1,3-benzoxazine-2,2'-tricyclo(3.3.1.1$^{3,7}$)decane]

Employing the procedure substantially as described in Example 3, Step C, but substituting for the 2-aminomethyl-4-(1,1-dimethylethyl)-6-trifluoromethylphenol used therein, an equimolar amount of 2-aminomethyl-4-[1-tricyclo(3.3.1.1$^{3,7}$)decyl]-6-iodophenol, there is produced 3,4-dihydro-6-[1-tricyclo(3.3.1.1.$^{3,7}$)decyl]-8-iodospiro[2H-1,3-benzoxazine-2,2'-tricyclo(3.3.1.1.$^{3,7}$)decane].

EXAMPLE 8

3,4-Dihydro-5,7-Dichloro-6,8-dimethylspiro[2H-1,3-benzoxazine-2,2'-tricyclo(3.3.1.1$^{3,7}$)decane]

Step A: Preparation of 2-chloro-N-[2-methoxy-3,5-dimethylphenyl]methyl acetamide To a solution of 2.72 g. (0.02 mole) of 2,4-dimethylanisole in 20 ml. of acetic acid and 2 ml. of sulfuric acid was added (2.47 g., 0.02 mole) 2-chloro-N-(hydroxymethyl)acetamide at <20° C. over a 10 minute period with stirring. After standing at room temperature about 20 hours the mixture was poured with stirring into 250 ml. of ice-water. After 1 hour the precipitate was collected, washed with water and dried at 60° C. and recrystallized 3 times from methanol:water (3:2), once from ethanol:water (3:2) and twice from ethanol:water (1:1) to give 0.34 g. of 2-chloro-N-[2-methoxy-3,5-dimethylphenyl]methyl acetamide, m.p. 124°–124.5° C.

Step B: Preparation of 2-chloro-N-[2-methoxy-3,5-dimethyl-4,6-dichlorophenyl]methylacetamide A stirred, intimate mixture of 2.42 g. (0.01 mole) of 2-chloro-N-[2-methoxy-3,5-dimethylphenyl]methylacetamide and 1.45 g. (0.011 mole) of aluminum chloride was treated with a mixture of 6 g. (0.044 mole) of sulfuryl chloride and 8 drops of sulfur monochloride. After stirring and heating on a steam bath for 1.5 hours, and cooling, there was added 200 ml. of 10% (v/v) hydrochloric acid. The precipitate was recrystallized 5 times from ethanol/water to give 0.25 g. of 2-chloro-N-[2-methoxy-3,5-dimethyl-4,6-dichlorophenyl]methylacetamide, m.p. 205°–206° C.

Step C: Preparation of 2-aminomethyl-3,5-dichloro-4,6-dimethylphenol

2-Chloro-N-[2-methoxy-3,5-dimethyl-4,6-dichlorophenyl]methylacetamide (1.6 g., 0.00515 mole) was refluxed with 20 ml. of 48% hydrobromic acid, and 20 ml. of acetic acid for 1.5 hours. After cooling to about 5° C., the precipitate was collected, washed with ether, dried at 60° C. to give 1.3 g. of 2-aminomethyl-3,5-dichloro-4,6-dimethylphenol hydrobromide, m.p. 305°–307° C. (dec.).

This material is converted to the free base by dissolving in 75 ml. of water and adding excess ammonium hydroxide.

Step D: Preparation of 3,4-dihydro-5,7-dichloro-6,8-dimethylspiro[2H-1,3-benzoxazine-2,2'-tricyclo(3.3.1.1$^{3,7}$)decane]

Employing the procedure substantially as described in Example 3, Step C, but substituting for the 2-aminomethyl-4-(1,1-dimethylethyl)-6-trifluoromethylphenol used therein, an equimolar amount of 2-aminomethyl-3,5-dichloro-4,6-dimethylphenol, there is produced 3,4-dihydro-5,7-dichloro-6,8-dimethylspiro[2H-1,3-benzoxazine-2,2'-tricyclo(3.3.1.1$^{3,7}$)decane].

EXAMPLE 9

3,4-Dihydro-6-(1,1-dimethylethyl)-8-iodospiro[2H-1,3-benzoxazine-2,1'-cyclohexane]

A mixture of 2-aminomethyl-4-(1,1-dimethylethyl)-6-iodophenol (1.5 g., 0.005 mole), cyclohexanone (0.5 g., 0.005 mole), and magnesium sulfate (0.5 g.) in tetrahydrofurane (50 ml.) is kept under nitrogen at 20°–25° C., for 16 hours. The magnesium sulfate is removed and the filtrate evaporated to dryness. The residue is crystallized from ethanol to obtain 3,4-dihydro-6-(1,1-dimethylethyl)-8-iodospiro[2H-1,3-benzoxazine-2,1'-cyclohexane] (1.4 g.), m.p. 112–114° C.

If in the above procedure the magnesium sulfate is replaced by an equal weight of molecular sieves, there is obtained 1.4 of 3,4-dihydro-6-(1,1-dimethylethyl)-8-iodospiro[2H-(1,3-benzoxazine-2,1'-cyclohexane], m.p. 112.5–114.5° C.

EXAMPLE 10

3,4-Dihydro-6-(1,1-dimethylethyl)-8-iodospiro[2H-(1,3-benzoxazine-2,2'-tricyclo(3.3.1.1$^{3,7}$)decane]

A mixture of 2-aminomethyl-4-(1,1-dimethylethyl)-6-iodophenol (1.5 g., 0.005 mole), 2-oxotricyclo(3.3.1.1$^{3,7}$)-decane (0.75 g., 0.005 mole) and p-toluenesulfonic acid (50 mg.) in benzene (25 ml.) is refluxed under a Dean-Stark trap for 2 hr. The solution is cooled, filtered, and evaporated to dryness. The residue is crystallized from ethanol to obtain 3,4-dihydro-6-1,1-dimethylethyl)-8-iodospiro[2H-(1,3-benzoxazine-2,2'-tricyclo(3.3.1.1$^{3,7}$)decane] (1.4 g.), m.p. 165°–166° C.

If the p-toluene sulfonic acid is omitted from the above reaction, there is obtained 1.8 g. of 3,4-dihydro-6-(1,1-dimethylethyl)-8-iodospiro[2H-1,3-benzoxazine-2,2'-tricyclo(3.3.1.1$^{3,7}$)decane], m.p. 162°–164° C.

If the aminomethylphenol in the above procedure (1.5 g.) and 2-adamantanone (0.75 g.) in dioxane (15 ml.) are refluxed under a Soxhlet extractor, in which the thimble is filled with molecular sieves, for 4 hr. and the mixture worked up in the same manner, there is obtained 3,4-dihydro-6-(1,1-dimethylethyl)-8-iodospiro[2H-1,3-benzoxazine-2,2'-tricyclo(3.3.3.1$^{3,7}$)decane] (1.4 g.), m.p. 162°–164° C.

EXAMPLE 11

3,4-Dihydro-6-chlorospiro[pyrido(3.2.h)-2H-1,3-benzoxazine-2,2'-tricyclo(3.3.1.1$^{3,7}$)decane]

Step A: Preparation of N-(5-chloro-8-hydroxy-6-quinolyl-methyl)phthalimide

N-(hydroxymethyl)phthalamide (19 g., 0.107 mole) is added portion-wise (1 hr.) at about 20° to a well stirred solution of 5-chloro-8-hydroquinoline (18 g., 0.1 mole) in conc. H$_2$SO$_4$ (200 ml.). Stirring at 20° is continued for 2½ hr. and then at 85°–90° for 25 hr. The cooled mixture then is stirred into ice-water, the aqueous mixture is adjusted to pH ca. 5 (NaOH and NaHCO$_3$). The precipitated imide is collected, dried and crystallized from benzene to obtain N-(5-chloro-8-hydroxy-6-quinolyl-methylphthalimide, m.p. 245°–247° C.

Step B: Preparation of 5-Chloro-7-aminomethyl-8-hydroxyquinoline dihydrochloride The imide prepared in Step A (34 g., 0.098 mole) is added to 12 N hydrochloric acid (2 l) and the mixture is refluxed for 52 hr. Th cooled mixture is filtered to remove the phthalic acid formed in the hydrolysis, concentrated to a small volume, and diluted with water. Upon neutralization with conc. NH$_4$OH a solid separates. This is crystallized from a mixture of water, ethanol and con. hydrochloric acid to obtain 5-chloro-7-aminomethyl-8-hydroxyquinoline dihydrochloride (15.5 g.), m.p. 237°–241° C. (dec).

Step C: Preparation of 3,4-Dihydro-6-chlorospiro[pyrido-(3.2.h)-2H-1,3-benzoxazine-2,2'-tricyclo-(3.3.1.1$^{3,7}$)decane]

A mixture of 5-chloro-7-aminomethyl-8-hydroxyquinoline (2.08 g., 0.01 mole), 2-oxotricyclo(3.3.1.1$^{3,7}$)-decane (1.5 g., 0.01 mole) and benzene (100 ml.) is refluxed under a Dean-Stark trap for 4 hrs. The solvent is evaporated and the residue is crystallized from benzene-hexane to obtain 3,4-dihydro-6-chlorospiro[-pyrido(3.2.h)-2H-1,3-benzoxazine-2,2'-tricyclo(3.3.1.1$^{3,7}$)decane] (2.3 g.) m.p. 146°-149° C.

EXAMPLE 12

3,4,3",4"'-Tetrahydro-6,6"-bis(1,1-dimethylethyl)-8,8"-diiododispiro[2H-1,3-benzoxazine-2,1'-cyclohexane-4',2"-2"H-1",3"-benzoxazine]

A mixture of 2-aminomethyl-4-(1,1-dimethylethyl)-6-iodophenol (3.0 g., 0.01 mole), of 1,4-cyclohexandione (0.36 g., 0.005 mole) and benzene (100 ml.) is refluxed under a Dean-Stark trap for 4 hr. The solvent is evaporated and the residue is crystallized from benzene to obtain 3,4,3",4"'-tetrahydro-6',6"-bis(1,1-dimethylethyl)-8,8"-diiododispiro[2H-1,3-benzoxazine-2,1'-cyclohexane-4',2"-2"H-1",3"-benzoxazine] (0.85 g.), m.p. 177°-178° C.

EXAMPLE 13

1. Tablets — 10,000 scored tablets for oral used, each containing 500 mg. of active ingredient are prepared from the following ingredients:

|  | Gm. |
| --- | --- |
| 3,4-dihydro-6-(1,1-dimethylethyl)-8-iodospiro[2H-1,3-benzoxazine-2,4'-tetrahydrothiopyran] | 5000 |
| Starch, U.S.P. | 350 |
| Talc, U.S.P,. | 250 |
| Calcium stearate | 35 |

The active ingredient is granulated with a 4% w./v. aqueous solution of methylcellulose U.S.P. (1500 cps). To the dried granules is added a mixture of the remainder of the ingredients and the final mixture compressed into tablets of proper weight.

2. Capsules — 10,000 two-piece hard gelatin capsules for oral use, each containing 250 mg. of active ingredient are prepared from the following ingredients:

|  | Gm. |
| --- | --- |
| 3,4-dihydro-6-(1,1-dimethylethyl)-8-iodospiro[2H-1,3-benzoxazine-2,1'-cyclohexane | 2500 |
| Lactose, U.S.P. | 1000 |
| Starch, U.S.P. | 300 |
| Talc, U.S.P. | 65 |
| Calcium Stearate | 25 |

The active ingredient is mixed with the starch lactose mixture followed by the talc and calcium stearate. The final mixture is then encapsulated in the usual manner. Capsules containing 10, 25, 50, and 100 mg. of active ingredient are also prepared by substituting 100, 250, 500, and 1000 gm. of 2500 gm. in the above formulation.

3. Soft elastic capsules - One-piece soft elastic capsules for oral use, each containing 500 mg. of active material are prepared in the usual manner by first dispersing the active material in sufficient corn oil to render the material capsulatable.

4. Aqueous suspension - An aqueous suspension for oral use containing in each 5 ml., 0.25 g. of active ingredient is prepared from the following ingredients:

|  | Gm. |
| --- | --- |
| 3,4-dihydro-6-(1,1-dimethylethyl)-8-iodospiro[2H-1,3-benzoxazine-Methylparaben, U.S.P. | 500 |
| Methylparaben, U.S.P. | 7.5 |
| Propylparaben, U.S.P. | 2.5 |
| Saccharin sodium | 12.5 |
| Glycerin | 3000 |

What is claimed is:

1. A method of treating an autoimmune disease selected from the group consisting of multiple sclerosis, and allergic encephalomyelitis which comprises oral or intravenous administration to a patient in need of such treatment from 1-50 mg/kg/day of a compound of formula:

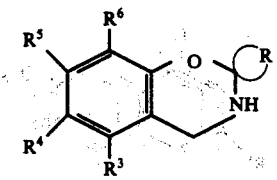

wherein
R$^3$ is
1. hydrogen,
2. methyl,
3. chloro, or
4. methoxy;
R$^4$ is
1. halo,
2. lower alkyl, or
3. adamantyl;
R$^5$ is
1. hydrogen,
2. lower alkyl,
3. lower alkoxy, or
4. halo;
R$^6$ is
1. halo,
2. lower alkyl,
3. lower alkylthio, or p2 4. trifluoromethyl;
R$^5$ and R$^6$ taken together is -N=CH-CH=CH-, and
R is
1. a spiro-carbocycle of 5,6, or 10-17 members, unsubstituted or substituted with
 a. lower alkyl,
 b. lower alkoxy,
 c. phenyl, or
 d. phenyl substituted with lower alkoxy, or
 e. lower alkanoyloxy;
2. a 6-membered spiroheterocycle containing 1 or 2 heteroatoms selected from the group consisting of oxygen, sulfur, and nitrogen wherein the nitrogen heteroatom can be substituted with lower alkyl, phenyl-lower alkyl, or lower alkanoyl;
3. a spiro-polycycloalkyl of 6-15 members, or 2. The method of claim 1 wherein the compound has structural formula:

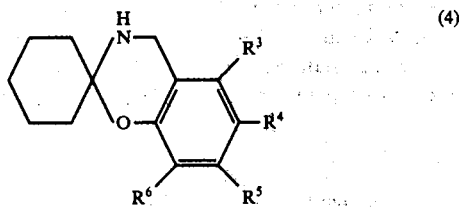
(4)

3. The method of claim 1 wherein the compound has structural formula:

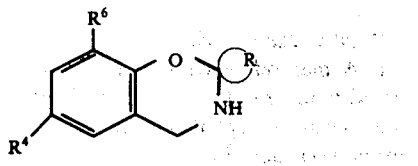

wherein $R^4$ is lower alkyl, $R^6$ is halo.

4. The method of claim 1 wherein the compound has structural formula:

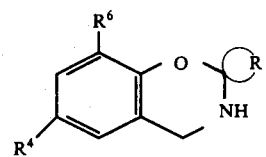

wherein $R^4$ is lower alkyl, $R^6$ is halo and

is spirotetrahydrothiapyan or spirocyclohexane.

5. The method of claim 1 wherein the compound is 3,4-dihydro-6-(1,1-dimethylethyl)-8-iodospiro[2H-1,3-benzoxazine-2,1'-cyclohexane].

6. The method of claim 1 wherein the compound is 3,4-dihydro-6-(1,1-dimethylethyl)-8-chlorospiro[2H-1,3-benzoxazine-2,1'-cyclohexane].

7. The method of claim 1 wherein the compound is 1'-methyl-3,4-dihydro-6-(1,1-dimethylethyl)-8-iodospiro[2H-1,3-benzoxazine-2,4'-piperidine].

8. The method of claim 1 wherein the compound is 3,4- dihydro-6-(1,1-dimethylethyl)-8-iodospiro[2H-1,3-benzoxazine-2,3'-tricyclo[2.2.1.0$^{2,6}$]heptane].

9. The method of claim 1 wherein the compound is 3,4-dihydro-6-(1,1-dimethylethyl)-8-iodospiro[2H-1,3-benzoxazine-2,2'-tricyclo[3.3.1.1$^{3,4}$]decane].

10. The method of claim 1 wherein the compound is 3,4-dihydro-6-(1,1-dimethylethyl)-8-iodospiro[2H-1,3-benzoxazine-2,4'-tetrahydrothiopyran].

* * * * *

UNITED STATES PATENT OFFICE
CERTIFICATE OF CORRECTION

Patent No. 4,070,464                    Dated January 24, 1978

Inventor(s) Edward J. Cragoe, Jr. et al.

It is certified that error appears in the above-identified patent and that said Letters Patent are hereby corrected as shown below:

Claim 1, column 14, line 52; "lower alkylthio, or p2 4. trifluoromethyl;" should be --- lower alkylthio, or 4. trifluoromethyl; ---

Claim 9, column 16, line 30;" [3.3.1.1$^{3,4}$]" should be --- [3.3.1.1$^{3,7}$] ---.

Signed and Sealed this

Twentieth Day of June 1978

[SEAL]

Attest:

RUTH C. MASON
Attesting Officer

DONALD W. BANNER
Commissioner of Patents and Trademarks